US00PP17000P2

(12) United States Plant Patent
Pieters

(10) Patent No.: US PP17,000 P2
(45) Date of Patent: Aug. 15, 2006

(54) ***CHRYSANTHEMUM* PLANT NAMED 'GEDI THREE PYEL'**

(50) Latin Name: *Chrysanthemum morifolium*
Varietal Denomination: Gedi Three Pyel

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 11/118,274

(22) Filed: Apr. 28, 2005

(51) Int. Cl.
*A01H 5/00* (2006.01)

(52) U.S. Cl. ..... Plt./295
(58) Field of Classification Search ..... Plt./295
See application file for complete search history.

(56) References Cited

U.S. PATENT DOCUMENTS

PP13,455 P2 1/2003 Pieters
PP13,797 P2 5/2003 Pieters
PP14,501 P2 2/2004 Pieters

OTHER PUBLICATIONS

Dowrick et al. "The induction of mutations in *Chrysanthemum* using x– and gamma radiation", 1966, Euphytica, 15:204–210.*

* cited by examiner

*Primary Examiner*—Kent Bell
*Assistant Examiner*—Annette H Para
(74) *Attorney, Agent, or Firm*—Knobbe Martens Olson & Bear, LLP

(57) ABSTRACT

A new and distinct *Chrysanthemum* plant cultivar is disclosed, characterized by a somewhat open-centered flower with bright yellow ray florets, and a mounding, free-branching growth habit. The new variety naturally blooms in the first two weeks of September.

1 Drawing Sheet

Figure 1:
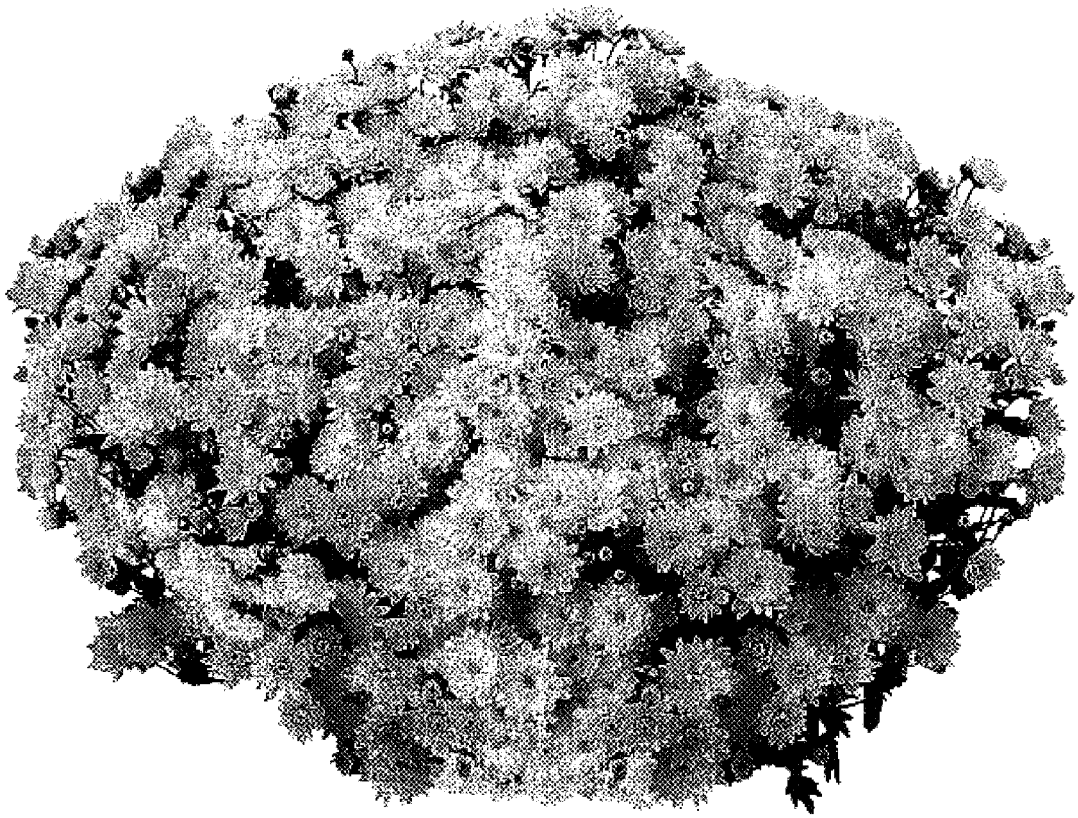

Latin name of the genus and species: *Chrysanthemum morifolium.*
Variety denomination: 'Gedi Three Pyel'.

BACKGROUND OF THE INVENTION

The new cultivar is the result of an induced mutation produced from the parent *Chrysanthemum* plant variety 'Gedi Two Pad' (U.S. Plant Pat. No. 14,501) using gamma ray treatment at a dose of 20 Gy. The new cultivar was discovered and selected by Dirk Pieters in a controlled environment in Oostnieuwkerke, Belgium, in September, 2002.

Asexual reproduction of the new cultivar 'Gedi Three Pyel' by terminal cuttings and tissue culture was performed in Oxnard, Calif., and has shown that the unique features of this cultivar are stable and reproduced true to type on successive generations.

SUMMARY OF THE INVENTION

The cultivar 'Gedi Three Pyel' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gedi Three Pyel.' These characteristics in combination distinguish 'Gedi Three Pyel' as a new and distinct *Chrysanthemum* cultivar:

1. The ray florets are bright yellow.
2. The flower has a somewhat open center.
3. The plant has a mounding growth habit.
4. The plant is free branching.

5. The plant has an early natural season bloom response in the first two weeks of September.

Plants of the new cultivar 'Gedi Three Pyel' are similar to plants of the parent variety, 'Gedi Two Pad,' in most horticultural characteristics. However, plants of the new cultivar have yellow ray florets, while the parent variety 'Gedi Two Pad' has pink ray florets.

In comparison to the commercially available variety 'Gedi One Avi' (U.S. Plant Pat. No. 13,455), the new variety 'Gedi Three Pyel' has less ray florets on each flower, and has approximately 12 more flowers per flowering branch.

In comparison to the commercially available variety 'Gedi One Ces' (U.S. Plant Pat. No. 13,797), the new variety 'Gedi Three Pyel' has approximately 9 more flowers per flowering branch, and has a wider but shorter leaf.

BRIEF DESCRIPTION OF THE PHOTOGRAPH

The accompanying photograph in FIG. 1 illustrates in full color a typical plant of 'Gedi Three Pyel' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'Gedi Three Pyel' plants grown in Oxnard, Calif., during the month of September, 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'Gedi Three Pyel.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 26 cm.
Plant spread: Approximately 32 cm.
Growth rate: Moderate.
Branching characteristics: Free branching.
Length of lateral branches: Approximately 21 cm.
Number of leaves per lateral branch: Approximately 16.
Age of plant described: Approximately 140 days from a rooted cutting.

FOLIAGE

Leaf:
*Arrangement.*—Alternate.
*Average length.*—Approximately 5.7 cm.
*Average width.*—Approximately 4.1 cm.
*Shape of blade.*—Ovate.
*Apex.*—Cuspidate.
*Base.*—Attenuate.
*Attachment.*—Stalked.
*Margin.*—Palmately lobed and toothed.
*Texture of top surface.*—Lightly pubescent.
*Texture of bottom surface.*—Lightly pubescent.
*Leaf internode length.*—Approximately 2.3 cm.
*Color.*—Young foliage upper side: Near Green 137A. Young foliage under side: Near Green 137A. Mature foliage upper side: Near Green 137A. Mature foliage under side: Near Green 137A.
*Leaf venation.*—Type: Palmately net. Venation color upper side: Near Green 138A. Venation color under side: Near Green 138A.
Petiole:
*Average length.*—Approximately 1.9 cm.
*Color.*—Near Green 138A.
*Diameter.*—Approximately 0.2 cm.

BLOOM

Flower:
*Flowering habit.*—Induced by darkness period greater than approximately 13.5 hours, approximately 45 days of appropriate day length required to induce and develop blooms.
*Form.*—Decorative.
*Natural flowering season.*—Approximately the first 2 weeks of September.
*Number of flowers per lateral branch.*—Approximately 24.
*Diameter.*—Approximately 5.8 cm.
*Depth.*—Approximately 2.0 cm.
*Longevity on plant.*—Approximately 26 days.
*Persistence.*—Persistent.
Ray florets:
*Appearance.*—Matte.
*Texture.*—Smooth.
*Average number of ray florets per flower.*—Approximately 155.
*Shape.*—Oblong.
*Aspect.*—Flat.
*Margin.*—Entire.
*Apex.*—Retuse.
*Length.*—Approximately 2.3 cm.
*Width.*—Approximately 1 cm.
*Color.*—Upper surface at first opening: Near Yellow 12B. Upper surface at maturity: Near Yellow 9A. Upper surface at fading: Near Yellow 9C. Under surface at first opening: Near Yellow 12A. Under surface at maturity: Near Yellow 6C. Under surface at fading: Near Yellow 5C.
Disc florets:
*Appearance.*—Shiny.
*Texture.*—Smooth.
*Average number of disc florets per disc.*—Approximately 15.
*Shape.*—Cylindric.
*Apex.*—Obtuse.
*Average length.*—Approximately 0.7 cm.
*Average width.*—Approximately 0.1 cm.
*Color.*—At first opening: Near Yellow 9B. At maturity: Near Yellow 9A. At fading: Near Yellow 13B.
Peduncle:
*Length.*—At terminal end (shortest): Approximately 2.7 cm. At lateral end (longest): Approximately 6.1 cm.
*Angle to stem.*—Acute.
*Strength.*—Moderate.
*Color.*—Near Green 137A.
*Habit.*—Upright.
*Diameter.*—Approximately 0.2 cm.
*Surface texture.*—Lightly pubescent.
Flower bud:
*Length.*—Approximately 0.9 cm.
*Diameter.*—Approximately 0.8 cm.
*Form.*—Globular.
*Color.*—Near Yellow 9A.
Involucral bracts (phyllaries):
*Appearance.*—Matte.
*Texture.*—Lightly pubescent.
*Number.*—Approximately 30.
*Shape.*—Oblanceolate.
*Margin.*—Entire.
*Apex.*—Acute.
*Length.*—Approximately 1 cm.
*Width.*—Approximately 0.9 cm.
*Color.*—Upper side: near Green 137A. Under side: near Green 137A.

REPRODUCTIVE ORGANS

Ray florets:
*Number of pistils per floret.*—1.
*Stigma shape.*—2 branched.
*Stigma color.*—Near Yellow 9C.
*Style color.*—Near Yellow 8C.
*Style length.*—Approximately 0.9 cm.
*Stamens.*—Absent.
Disc florets:
*Number of pistils per florets.*—1.
*Stigma shape.*—Two-branched.
*Stigma color.*—Near Yellow 6D.
*Style length.*—Approximately 0.3 cm.
*Style color.*—Near Yellow 4C.

*Number of stamens per floret.*—Approximately 5.
*Anther shape.*—Tubular.
*Anther color.*—Near Yellow 12A.
*Pollen color.*—Near Yellow 12A.

OTHER CHARACTERISTICS

Disease resistance: Neither resistance nor susceptibility has been observed in this variety.

Drought tolerance/cold tolerance: Flowering plants are hardy to a low temperature of about −2° C. Non-flowering plants are hardy in the approximate range of 3° C. to −6° C., depending upon duration of cold an amount of moisture in the soil. With adequate water plants are hardy to a high temperature of about 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'Gedi Three Pyel' as herein illustrated and described.

* * * * *